United States Patent [19]

Leugers et al.

[11] Patent Number: 5,125,749
[45] Date of Patent: Jun. 30, 1992

[54] PROBE FOR PHOTOACOUSTIC ANALYSIS

[75] Inventors: Mary A. Leugers; Michael E. Mills, both of Midland, Mich.

[73] Assignee: The Dow Chemical Company, Midland, Mich.

[21] Appl. No.: 586,668

[22] Filed: Sep. 24, 1990

[51] Int. Cl.⁵ .......................................... G01N 21/00
[52] U.S. Cl. .................................... 356/432; 356/72; 436/174; 359/285; 367/140
[58] Field of Search ............... 356/432, 432 T, 73, 356/72; 73/24, 643; 250/339, 306, 308, 334; 422/80.05, 68.1; 436/174; 72/606, 602; 359/285; 367/140

[56] References Cited

U.S. PATENT DOCUMENTS

| | | | |
|---|---|---|---|
| 3,938,365 | 2/1976 | Dewey, Jr. | 73/24 |
| 3,948,345 | 4/1976 | Rosencwaig | 181/0.5 |
| 4,028,932 | 6/1977 | Rosencwaig | 73/61.2 |
| 4,163,382 | 8/1979 | Amer | 73/24 |
| 4,255,971 | 3/1981 | Rosencwaig | 73/606 |
| 4,267,732 | 5/1981 | Quate | 73/606 |
| 4,276,780 | 7/1981 | Patel et al. | 73/643 |
| 4,379,409 | 4/1983 | Primbsch et al. | 73/643 |
| 4,408,478 | 10/1983 | Bechthold et al. | 73/24 |
| 4,512,197 | 4/1985 | von Gutfeld et al. | 73/643 |
| 4,516,853 | 5/1985 | Pearson | 356/152 |
| 4,543,486 | 9/1985 | Rose | 250/492.1 |
| 4,567,769 | 2/1986 | Barkhoudarian | 73/643 |
| 4,663,961 | 5/1987 | Nelson et al. | 73/24 |

FOREIGN PATENT DOCUMENTS 2709725 9/1978 Fed. Rep. of Germany .
2089041 6/1982 United Kingdom .

OTHER PUBLICATIONS

"Nitric Oxide Air Pollution: Detection by Optoacoustic Spectroscopy", SCIENCE, vol. 173, Jul. 2 1971, pp. 45–47.
Rosencwaig, A., "Photoacoustic Spectroscopy of Solids", OPTICS COMMUNICATIONS, vol. 7, No. 4, Apr. 1973, pp. 305–308.
von Gutfeld, R. J., Melcher, R. L., "20-MHz acoustic waves from pulsed thermoelastic expansions of constrained surfaces", APPLIED PHYSICS LETTERS, vol. 30, No. 6, Mar. 15 1977, 257–259.
Rosencwaig, A., "Photoacoustic Spectroscopy of Solids", ULTRASONICS SYMPOSIUM PROCEEDINGS, Oct. 26–28 1977, 337–343.
Farrow, J. M., Burnham, R. K., Auzanneau, M., Olsen, S. L., Purdie, N., Eyring E. M., "Piezoelectric detection of photoacoustic signals", APPLIED OPTICS, vol. 17, No. 7, Apr. 1978, 1093–1098.
Wong, Y. H., Thomas, R. L., Hawkins, G. F., "Surface and subsurface structure of solids by laser photoacoustic spectroscopy", APPLIED PHYSICS LETTERS, 32(9), May 1 1978, 538–539.
"A Toxic Gas Monitor with ppb Sensitivity Using an Automated Laser Optoacoustic Spectrometer", LASER IN DER PRAXIS, pp. 18–19 Nr. 2, 1979, vol. II.
Patel, C. K. N., Tam, A. C., "Pulsed optoacoustic spectroscopy of condensed matter", REVIEWS OF MODERN PHYSICS, vol. 53, No. 3, Jul. 1981, 517–550.
Leslie, D. H., Trusby, G. L. Dandridge, H. Giallerenzi, T. C., "FIBRE-OPTIC SPECTROPHONE", ELECTRONICS LETTER, vol. 17, No. 17, Aug. 20, 1981, pp. 581–582.

(List continued on next page.)

Primary Examiner—Vincent P. McGraw
Assistant Examiner—LaCharles P. Keesee, II
Attorney, Agent, or Firm—Timothy S. Stevens

[57] ABSTRACT

A probe for in situ quantitative detection of the concentration of an analyte in a sample includes a hollow elongated body adapted for single ended contact with the sample. The body has at least one optical fiber extended through the body for transmitting modulated light through the body, out a window at the forward end of the body, and along an optical axis into the sample to optically excite the analyte. A pressure transducer mounted beyond the window and spaced laterally away from the optical axis detects an acoustic response of the analyte to the modulated light. This probe is particularly suitable for performing remote photoacoustic analysis of analyte concentration in a sample.

18 Claims, 6 Drawing Sheets

OTHER PUBLICATIONS

DePaula, R. P., Flax, L., Cole, J. H., Bucaro, J. A., "Single-Mode Fiber Ultrasonic Sensor", IEEE JOURNAL OF QUANTUM ELECTRONICS, vol. QE-18, No. 4, Apr. 1982.

Bowers, J. E., "Fiber-optical sensor for surface acoustic waves", APPLIED PHYSICS LETTERS 41(3), Aug. 1982, pp. 231-233.

West, G. A., Barrett, J. J., Siebert, D. R., Reddy, K. V., "Photoacoustic spectroscopy", REV. SCI. INSTRUM., 54(7), Jul. 1981, pp. 797-817.

PASFLUORENEA  10R x 5C

| 0 | 1 TOTAL VOLUME 2,4D SOL'N | 2 CONCENTRATION PPM | 3 PAS P-P | 4 LASER P-P | 5 NORMALIZED PAS |
|---|---|---|---|---|---|
| 1 | 0 | 0.00 | 5.960 | 2.397 | 0.402181 |
| 2 | 0 | 0.00 | 5.952 | 2.366 | 0.397513 |
| 3 | 2 | 2.14 | 4.124 | 3.148 | 0.763337 |
| 4 | 3 | 3.21 | 3.514 | 2.888 | 0.821855 |
| 5 | 4 | 4.28 | 3.569 | 2.943 | 0.824601 |
| 6 | 6 | 6.42 | 3.758 | 3.152 | 0.838744 |
| 7 | 11 | 11.77 | 3.926 | 3.555 | 0.905502 |
| 8 | 21 | 22.47 | 3.979 | 3.885 | 0.976376 |
| 9 | 31 | 33.17 | 4.190 | 4.083 | 0.974463 |
| 10 | 56 | 59.92 | 4.318 | 4.010 | 0.928671 |

PASFLUORENE 12R x 5C

| | 1 total vol fluorene sol'n | 2 PAS P-P (V) | 3 LASER P-P (V) | 4 NORMALIZED PAS | 5 CONCENTRATION FLUORENE (PPM) |
|---|---|---|---|---|---|
| 1 | 0 | 1.710 | 1.3060 | 1.309342 | 0.000000 |
| 2 | 2 | 1.836 | 1.3350 | 1.375281 | 0.213985 |
| 3 | 4 | 1.933 | 1.3140 | 1.471081 | 0.427970 |
| 4 | 6 | 2.056 | 1.2440 | 1.652733 | 0.641955 |
| 5 | 8 | 2.055 | 1.1220 | 1.831551 | 0.855939 |
| 6 | 13 | 2.108 | 1.0600 | 1.988679 | 1.390901 |
| 7 | 18 | 2.231 | 1.0160 | 2.195866 | 1.925864 |
| 8 | 28 | 2.353 | 0.9459 | 2.487578 | 2.995788 |
| 9 | 48 | 2.664 | 0.9495 | 2.805687 | 5.135636 |
| 10 | 68 | 2.708 | 0.9237 | 2.931688 | 7.275484 |
| 11 | 108 | 2.670 | 0.8980 | 2.973274 | 11.555181 |
| 12 | 158 | 2.390 | 0.8456 | 2.826395 | 16.904802 |

FIGURE 9

PAS24DNAOH 14R x 5C

| 0 | 1 TOTAL VOL 2,4D (UL) | 2 CONCENTRATION 2,4D PPM | 3 PAS P-P | 4 LASER P-P | 5 NORMALIZED PAS |
|---|---|---|---|---|---|
| 1 | 0 | 0.0000 | 47.00 | 0.6594 | 71.276918 |
| 2 | 0 | 0.0000 | 34.50 | 0.6164 | 55.970149 |
| 3 | 1 | 0.2746 | 34.20 | 0.6169 | 55.438483 |
| 4 | 2 | 0.5492 | 38.33 | 0.6195 | 61.872478 |
| 5 | 4 | 1.0984 | 40.41 | 0.6410 | 63.042122 |
| 6 | 8 | 2.1968 | 27.95 | 0.6454 | 43.306477 |
| 7 | 18 | 4.9428 | 33.51 | 0.6201 | 54.039671 |
| 8 | 38 | 10.4348 | 40.99 | 0.6214 | 65.963952 |
| 9 | 78 | 21.4188 | 48.07 | 0.6112 | 78.648560 |
| 10 | 128 | 35.1488 | 49.50 | 0.5741 | 86.221913 |
| 11 | 228 | 62.6088 | 52.16 | 0.5701 | 91.492721 |
| 12 | 478 | 131.2588 | 73.70 | 0.5660 | 130.212014 |
| 13 | 978 | 268.5588 | 87.19 | 0.5653 | 154.236688 |
| 14 | 1978 | 543.1588 | 73.52 | 0.5550 | 132.468468 |

FIG. 10

PROBE FOR PHOTOACOUSTIC ANALYSIS

FIELD OF THE INVENTION

This invention relates to the determination of the concentration of an analyte in a sample, and more particularly, to a probe for optically exciting a sample and then detecting the photoacoustic response of a light absorbing analyte in the sample to determine its concentration.

BACKGROUND OF THE INVENTION

In many industrial applications, it is necessary to detect a concentration of an analyte in a sample, the sample being a liquid, gas or solid and the concentrations ranging from parts per billion to 100%. This invention relates to the remote detection and subsequent quantitative analysis that is necessary to determine the concentration of an analyte in a sample. Remote detection and analysis is typically necessary when, due to the chemical makeup of the sample or the commercial application for the analyte, intrusive or invasive detection and analysis would be either impractical or dangerous.

One method of detecting concentrations of an analyte in a sample is referred to as photoacoustic detection. In photoacoustic detection, the concentration of an analyte in a sample is detected by measuring the acoustic response of the sample after excitation by a modulated incident light of known wavelength. The magnitude of the acoustically detected signal corresponds to the concentration of the analyte within the sample. As the concentration of an analyte within the sample increases, an acoustic response of greater magnitude will be detected. By establishing a reference magnitude for a known concentration of a particular analyte in a particular sample, other unknown concentrations of the same analyte and sample can be subsequently determined.

There are a number of practical limitations associated with photoacoustic detection of an analyte in a sample, particularly if the sample is a flowing liquid or gas. For instance, it can be extremely difficult to direct a modulated incident light into a flowing sample in a manner which produces a "clean," photoacoustically detectable signal. Many attempts to provide a sufficiently clean signal involve routing of the sample through an isolated chamber and then returning the sample to its normal flow path, with optical excitation and photoacoustic detection occurring in the chamber. This enables detection of a component concentration in a liquid sample while it is in a flowing state. U.K. patent application No. 2,089,041A discloses such a device.

For many volatile and/or dangerous solutions, tapping into the sample or rerouting the flow path of the sample in this manner can be extremely cumbersome and/or expensive. However, unless the sample can be isolated in this manner, or in a similar manner, it is difficult to coordinate the direction of modulated light into the sample in a manner that will produce a clean photoacoustic response signal.

It is therefore an object of this invention to provide an improved apparatus and method for remotely directing modulated light into a sample to photoacoustically detect low concentrations of an analyte within the sample.

It is another object of the invention to provide an apparatus and method for non-invasive, accurate photoacoustic detection of the concentration of an analyte in a volatile and/or dangerous sample without requiring sample re-routing or removal.

It is still another object of the invention to provide a relatively inexpensive, improved apparatus and method for effectively and conveniently coordinating optical excitation and acoustic detection of a sample in order to quantitatively measure low concentrations of an analyte in the sample.

SUMMARY OF THE INVENTION

This invention contemplates a single ended probe for directing modulated light into a sample through optical fibers and detecting the photoacoustic response of a light absorbing analyte within the sample to determine the concentration of the analyte.

To these ends a preferred embodiment of the invention includes a single ended photoacoustic probe having an elongated, hollow cylindrical body with a cap located at a forward end. The cap has a lens serving as a window, and the cap further includes a longitudinal hollow, annulus portion that extends beyond the window. A piezoelectric transducer is housed in the annulus portion. One end of an electrical conductor is connected to the transducer and the other end of the conductor is connected to a preamplifier, which is in turn connected to one vertical input of an oscilloscope. One of the branch ends of a bifurcated fiberoptic cable extends through the probe body along an optical axis and terminates short of the window/lens. The other of the branch ends of the bifurcated cable is operatively connected to a photodiode, which is in turn connected to a second vertical input channel of the oscilloscope. A xenon flash lamp is operatively connected to the trunk of the fiberoptic cable for transmitting modulated light therealong to both the probe and the photodiode.

During analysis, the probe is placed in direct contact with a sample in order to measure the concentration of a light absorbing analyte in the sample. The xenon-flash lamp generates modulated light that is transmitted along one branch of the fiberoptic cable within the probe body, out of the lens along the optical axis and into the sample. The absorbed, modulated light produces non-radiative energy in the analyte, resulting in acoustic pulses. The piezoelectric transducer mounted within the annulus portion of the cap detects these pulses and generates an electrical signal in response thereto. The pulse-generated electrical signal is routed rearwardly through the body by the electrical leads to the preamplifier for amplification and subsequent input to the oscilloscope. Simultaneously, an electrical signal generated by the modulated light detected by the photodiode is also input to the oscilloscope for comparison with the pulse generated electrical signal.

By comparing the voltage amplitude (i.e., vertical peak-to-peak voltage) of the pulse or acoustically generated electrical signal with the voltage amplitude of the electrical signal obtained via the photodiode, a reference normalization value can be obtained. By plotting enough reference normalization values for various known concentrations of a particular analyte in a particular sample, a reference normalization curve can be plotted for a relatively wide range of concentrations. Subsequently, by normalizing the photodiode detected signal with respect to the photoacoustically detected signal from a sample of unknown concentration, the measured normalized value for the unknown concentration may be compared to the reference curve to determine the unknown concentration. Preferably, the reference normalization values used to obtain the reference curve are obtained by averaging the measured values from a number of tests.

This probe is capable of detecting analyte concentrations in a sample ranging from one hundred percent down to a few parts per million. Compared to other forms of transmission spectroscopy, this probe provides equivalent sensitivity ranges within a shorter optical transmission length. For these reasons, the probe is simpler to use and is less expensive. Compared to other photoacoustic probes, this probe facilitates remote sample analysis because it does not require rerouting or extracting of the sample from a flow line. A single ended probe body is used to both direct the modulated light into the sample and to acoustically detect the sample response, and therefore measurements can be made in situ within the sample to provide real-time monitoring in a processing environment. Because the relationship between actual concentration and normalized value (i.e., obtained from the photodiode and photoacoustic signals) has been found to be substantially linear for a frequently used, operable range of concentrations, the use of the probe requires very little signal interpretation or computation on the part of an operator.

According to another feature of the invention, the probe may be used to prepare a sample having a desired concentration of a known analyte. This can be accomplished by adding an analyte to a sample, during monitoring with the single-ended probe, until a normalization value calculated from measured photodiode and photoacoustic values becomes equal to a reference normalization value corresponding to a desired concentration.

Alternately, two probes may be used to prepare a second volume of a sample that is equal in analyte concentration to a first volume of the same sample. Each probe is initially zeroed independently in a reference solution, then zeroed again simultaneously in the first volume of the sample of the desired concentration. Subsequently, one of the probes is inserted into a second volume of the sample (of lower analyte concentration) while the other of the probes remains in the first volume. Thereafter, analyte is added to the second volume until the voltage amplitude difference between the photoacoustically generated electrical signals becomes zero.

One particularly useful and practical application for this photoacoustic probe includes the detection and monitoring of low concentrations of herbicides like 2, 4 Dichlorophenoxyacetic acid [2,4-D] in ground water run off occurring in agricultural lands.

These and other features of the invention will be more readily understood in view of the drawings, and the following detailed description of a preferred embodiment of the invention.

DETAILED DESCRIPTION OF THE INVENTION

Figures 1, 2:
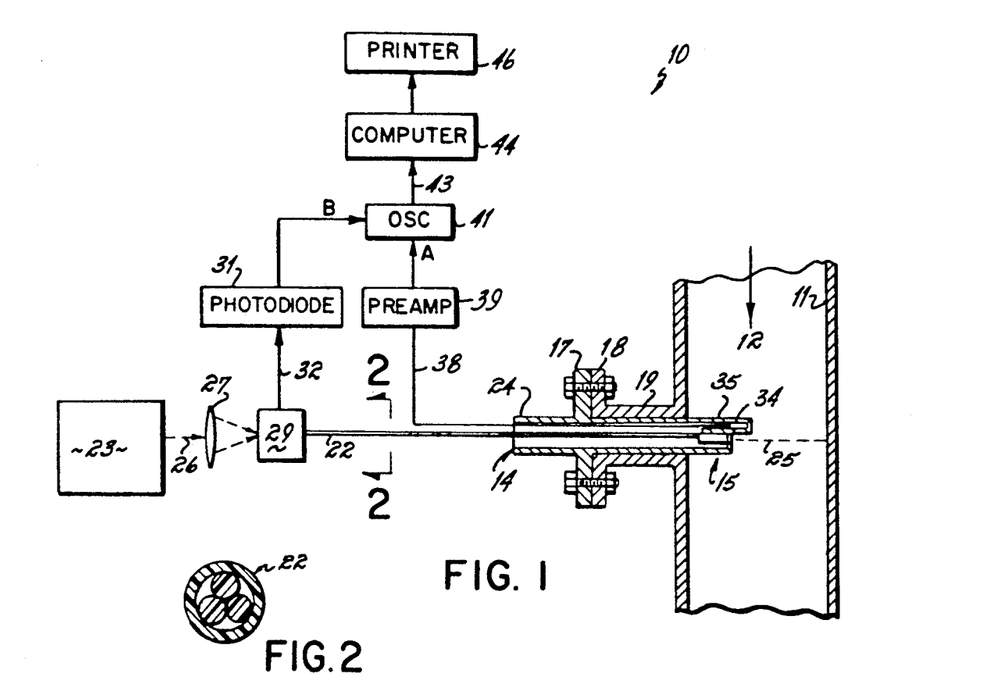
FIG. 1 is a schematic showing the components of a photoacoustic analysis system in accordance with a preferred embodiment of the invention.
FIG. 2 is a cross-sectional view taken along line 2—2 of FIG. 1.

FIG. 1 illustrates a preferred embodiment of the invention comprising a photoacoustic detection system 10 useful for determining the concentration of an analyte in a liquid sample 12 flowing through a pipe 11, for example. For this purpose, a single end of the probe 13 is placed directly in contact with the sample 12. The probe 13 includes an elongated, hollow body 14 with a length of about 12 inches, with a first or forward end 15 extending into the pipe 1 and in contact with the sample 12. According to this embodiment, the probe 13 includes a flange 17 bolted to a flange 18 of an outlet port 19 in the pipe 11. During times when analysis is not taking place, the body 14 may be withdrawn and outlet port 19 capped off, or plugged in any suitable manner to prevent leakage. Alternately, if desired, the probe body 14 alone may remain in place in the pipe 11, with the other components of the system 10 inserted into the body 14 and connected only when analysis is to take place.

During analysis, light directed from the flash lamp 23 initially follows a path indicated by directional arrow 26 onto a lens 27, preferably a 25.0 mm plano-convex silica lens such as a Melles Griot, Model LQP 177. This lens 27 focuses the light upon a wide gap 225 nm filter 29. Some of the light is conveyed via a fiberoptic cable 22 through a rearward end 24 of the body 14, along the body 14, through a window (not shown in FIG. 1) located at forward end 15, and into the sample along an optical axis 25. Additionally, a portion of the light from the source 23 is also conveyed by a fiber or fiber cable 32 to a photodiode 31, which is connected to an input of one of the vertical channels of an oscilloscope 41. Preferably, a bifurcated cable is used, with the trunk end of the cable connected to filter 29 and cable 32 serving as one branch for directing modulated light to photodiode 31 and cable 22 serving as the other branch for directing the modulated light to the probe 14. The filter 29 prevents individual fibers of cables 22 and 32 from degrading due to prolonged UV exposure. The individual fibers of the fiber cables 22 and 32 may be of various thicknesses. Moreover, cables containing any number of optical fibers may be used, although a single optical fiber with a single insulation tube seems to provide optimum results.

The flash lamp 23 may be a short arc (3 mm) Xenon-flash lamp made by EG&G, sold as Model No. 2P-3, which has a UV-Vis rich spectrum (200-1100 nm). The power supply for flash lamp 23 may be an EG&G power supply (not shown), Model No. PS-450, which provides a high voltage output of 950 volts. Flash durations of 10 microseconds may be obtained by discharging 5.5 joules of energy to the bulb of the flash lamp 23 from an external 12 microfarad capacitor (not shown). A Dynascan square wave generator, Model No. 3020 (not shown), may be used to send trigger pulses to the flash lamp 23 via the power supply and trigger an EG&G "Lite Pac" transformer, Model No. FY-900. This set up provides trigger pulses with a 5.0 volt DC amplitude, a 200 microsecond duration, and 200 millisecond delay times. Typical flashrates of 3–5 Hz may be achieved by setting the frequency dial of the square wave generator to $0.15-0.25 \times 10^4$ kHz. Because long term (1 min) average power with this set up is limited to 60 watts, flashrates will never exceed 10 Hz.

Preferably a Hoffman enclosure made from fourteen gauge steel serves as a radio frequency grounded shield for the flash lamp 23 assembly. If utilized, such an enclosure should be modified to include louvers and fans in the side walls to provide forced air cooling for the flash lamp 23 and trigger transformer. Otherwise, the components may fail to operate at temperatures above 60° C.

The directing of modulated light into the sample generates a sound wave or pulse in a light absorbing analyte within the sample. The sound waves are detected by a pressure transducer 34, preferably a piezoelectric detector, which is located beyond the window and is spaced laterally away from the optical axis 25. A Vernitron model PZT-5A may be used. A transducer of this type employs a sensor of lead titinate-zirconate piezoelectric ceramic, with silvered faces.

In response to acoustic detection, the transducer 34 generates an electrical signal that is relayed through the body 14 by an electrical lead 38 for input into a preamplifier 39, which may be a Tektronix model AM502. The amplified signal is then input to one of the vertical channels of the signal processor, such as a waveform processing oscilloscope 41. A Tektronix model 7854 oscilloscope may be used. A voltage corresponding to the acoustically detected response can be displayed and measured on the oscilloscope 41, and subsequently transmitted via an electrical cable 43 to a computer 44. If desired, the time varying voltage may be recorded or stored by the computer 44 and subsequently printed by a printer 46 connected to the computer 44.

As mentioned previously, the output of the photodiode 31 is also input to one of the vertical channels of the oscilloscope 41. The acoustically detected waveforms obtained from the probe 14 typically comprise several superimposed frequencies that are proportional to the pipe 11 dimensions or the dimensions of a cell which holds the sample. The amplitudes of the high frequency (150 kHz) acoustically detected waveforms may be used for concentration measurements by normalizing these waveforms against the amplitude of the photodiode-generated electrical signal.

Figure 3:
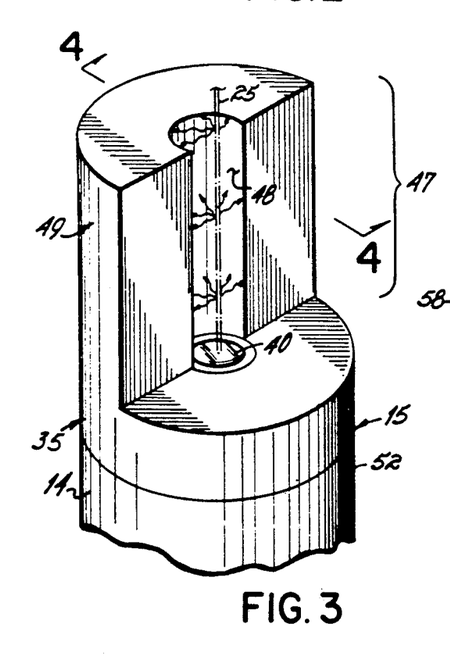
FIG. 3 is an enlarged view of a single ended probe depicted in FIG. 1.

FIG. 3 depicts, in greater detail, a preferred embodiment of the forward end 15 of probe 14. As shown, both the window and the transducer 34 are housed within a cap 35 located at the forward end 15 of the probe 14. The cap 35 may be integrally formed with the body 14 or simply connectable thereto. Preferably, both the cap 35 and the body 14 are of stainless steel, and the cap 35 is threadably connected to forward end 15. A window 40 or lens 10 is located in the center of the cap 35 in alignment with optical axis 25. The lens 40 is preferably plano convex in shape, made of sapphire and has a thickness of about 5 mm with a focal length of about 9 mm. The lens 40 reduces light beam divergence, or collimates the light, as it is directed into the sample. The cap 35 also includes a longitudinal, hollow, annulus portion 47 that extends beyond lens 40 and which houses the transducer 34. The annulus portion 47 has longitudinally extending inner 48 and outer 49 semicircular shaped walls. Preferably, annulus portion 47 has a longitudinal dimension of about 0.58", and the radial distance between wall 48 and wall 49 is about 0.31". This places inner wall 48 a radial distance of about 0.19" from optical axis 25.

Figure 4:
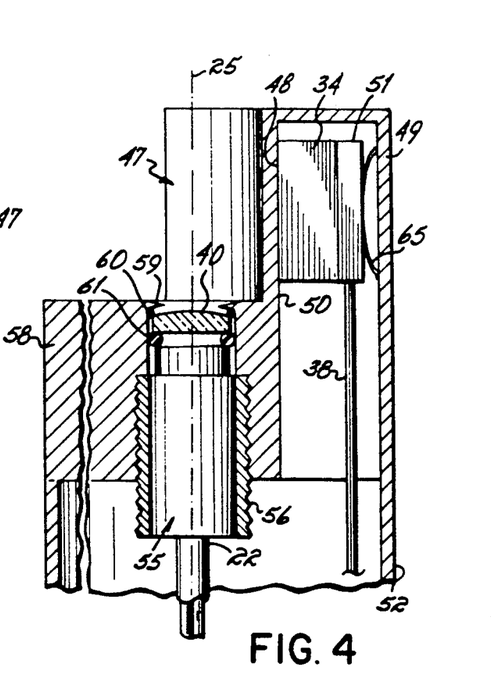
FIG. 4 is a cross sectional view taken along lines 3—3 of FIG. 2.

As shown more clearly in FIG. 4, the piezoelectric transducer 34 is mounted flush against a backside surface 50 of the inner wall 48, and is oriented perpendicular to optical axis 25, thereby optimizing acoustic sensitivity. The transducer 34 is preferably held against back side surface 50 by a leaf spring 65. The transducer 34 is also mounted to a lead backing 51 that is connected to an electrical lead 38 which extends along the length of the probe body 14 and out rearward end 24. In order to measure a voltage, or a potential difference with respect to ground, a second lead (not shown) serves as the ground reference and is connected separately to ah outer surface 52 of the probe body 14, proximate rearward end 24.

The fiberoptic cable 2 extends through body 14 into a hollow mounting ring 55 which is frictionally held on its external surface by another ring 56 that threadably connects within a core section 58 of the cap 35. The sapphire lens 40 is held in place by a circular flange 59 at the forward end of core 58 and by two O-rings 60 and 61. This overall structure places the lens 40 about 9 mm, i.e., its focal length, from the end of cable 22, and it also prevents sample leakage into the probe body 14. Moreover, O-rings 60 and 61 acoustically isolate the light delivery system to substantially reduce adverse effects that may otherwise be caused by undesired photoacoustic detection of scattered light transmitted through the fiber bundle 22.

Figure 5:
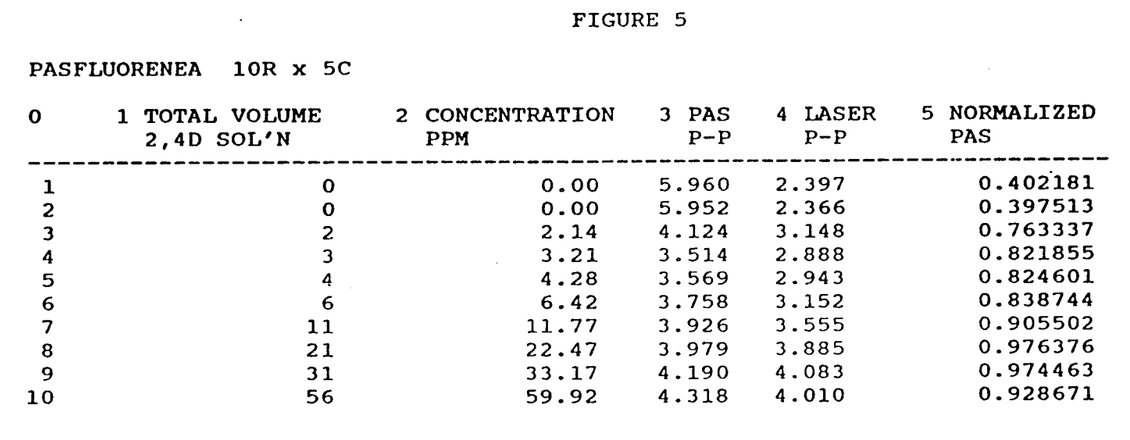
FIG. 5 is a table which shows concentration values of fluorene in a methanol solution and normalized photoacoustically detected voltage values for the same solution.
Figure 6:
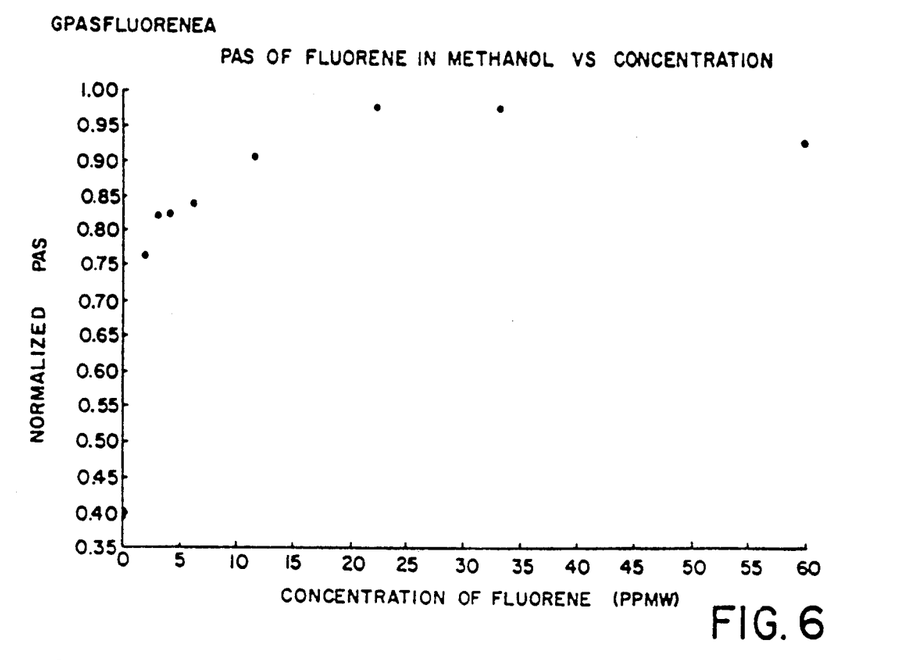
FIG. 6 graphically depicts the concentration values versus the normalized values of FIG. 5.
Figure 7:
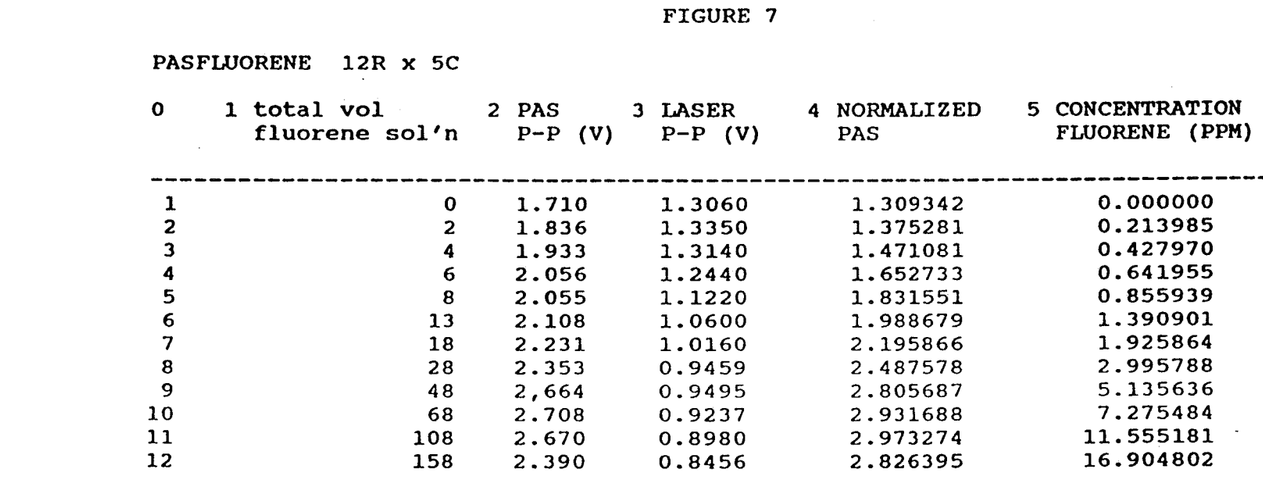
FIG. 7 is a table which shows concentration of fluorene in another prepared solution of methanol and normalized photoacoustically detected voltage values for the same solution.
Figure 8:
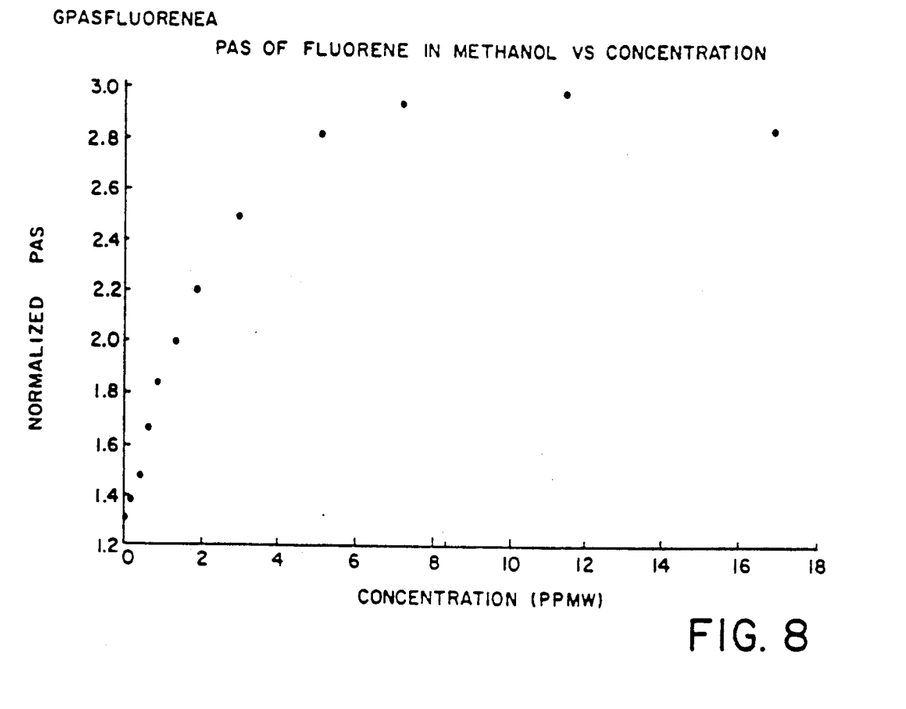
FIG. 8 is a graph depicting the concentration values versus the normalized values of FIG. 7.
Figure 9:
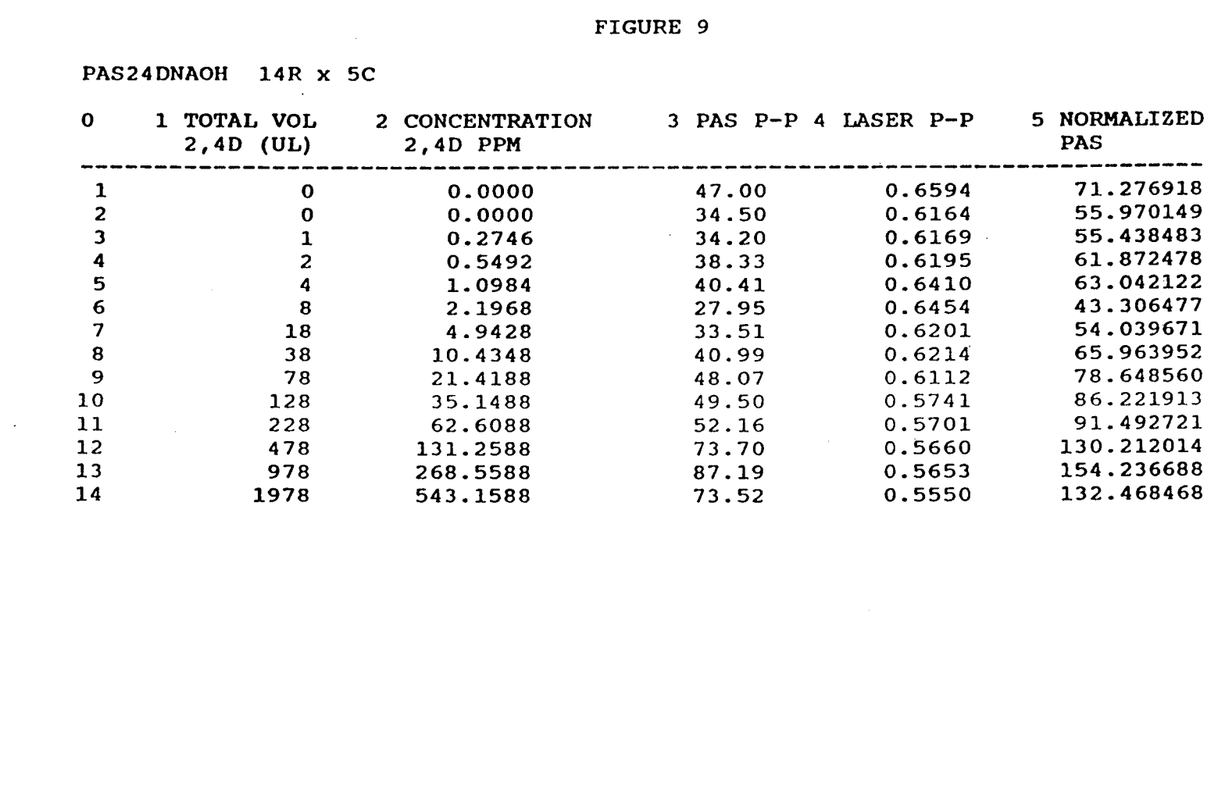
FIG. 9 is a table which shows concentration values of 2,4-dichlorophenoxyacetic acid in a sodium hydroxide solution and normalized photoacoustically detected voltage values for the same solution.
Figure 10:
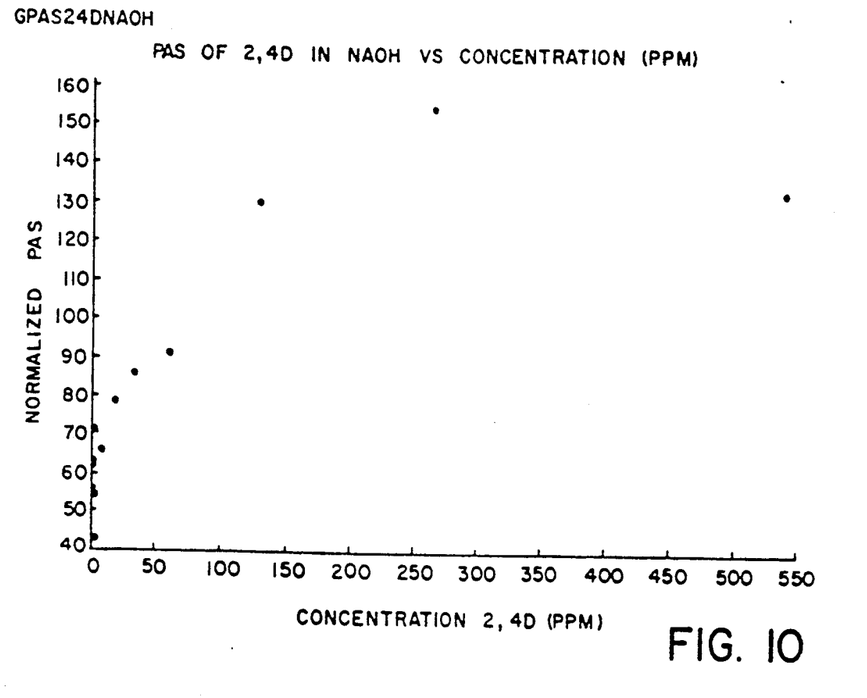
FIG. 10 graphically depicts the concentration versus the photoacoustically detected values of FIG. 9.

FIGS. 5, 7 and 9 are tables which show results obtained with a probe 10 in accordance with a preferred embodiment of the invention, as described herein. Column 0 represents the trial number. Column 1 represents the total volume of the sample solution used for the particular trial. Column 2 shows the known analyte concentration in the sample volume. Column 4 shows the photoacoustically detected peak-to-peak voltage amplitudes. Column 4 shows peak-to-peak voltage amplitudes obtained via the photodiode, and column 5 represents normalized values, i.e., column 4 divided by column 3. FIGS. 6, 8 and 10 graphically depict the known sample concentrations versus the normalized values shown in column 5 for FIGS. 5, 7 and 9, respectively. FIGS. 5-8 show results obtained from concentrated stock solutions of fluorene in methanol (0.71 wt %). FIGS. 9 and 10 show results obtained with 2,4-dichlorophenoxyacetic acid [2,4-D] (2.41 wt %) in 5% NAOH water. The graphs confirm, for a frequently used, operable range of analyte concentrations, a substantially linear relationship between prepared solution concentration and the normalized values obtained from measured photoacoustic and photodiode values.

As mentioned previously, these charts and/or graphs may be used to assist in subsequent photo-acoustic detection of analyte concentration in a sample. Moreover, the plotted reference curve may also be used to prepare samples having a desired analyte concentration level.

Although the probe 13 as shown in FIG. 1 is adapted for in-line photoacoustic analysis of a liquid sample flowing through the pipe 11, it is to be understood that the forward probe end 15 could also be placed directly in a non-flowing pool of the liquid sample, or the probe body 14 mounted to an enclosed, sample holding device or cell. Additionally, the forward probe end 15 could be positioned in contact with either a solid sample or a gas sample. In the case where a gas sample is to be monitored, as in stack emissions or perimeter monitoring, a microphone would be the preferred pressure transducer rather than the piezoelectric sensor.

Moreover, it is understood this invention also contemplates various other acoustic and sensor configurations. One advantage associated with the particular embodiment of the invention shown in FIGS. 1, 3 and 4 relates to the fact that the acoustic sensor geometry substantially matches the optically-generated acoustic wave geometry. That is, the semicircular shape of the sensor places all points on its surface substantially equidistant from the optical axis traversed by the light beam, thereby maximizing sensitivity. Nevertheless, numerous other geometric orientations of the acoustic sensor with respect to the optical axis would be suitable, and within the scope of the claims.

While a preferred embodiment of the invention has been described, other modifications and advantages will become readily apparent to one of ordinary skill in the art without departing from the scope of the invention, and applicant intends to be bound only by the claims appended hereto.

I claim:

1. A probe for photoacoustic analysis of a sample, comprising:
    a hollow body having forward and rearward ends;
    an optical fiber extended through the body for directing modulated light out of a window at said forward end and into the sample along an optical axis; and
    photoacoustic detection means extended through the body to a position located beyond said window and proximate to said optical axis for detecting an acoustic response of the sample to said modulated light.

2. The probe of claim 1 wherein said photoacoustic detection means includes a pressure transducer and further comprising:
    a cap connectable to said forward end, the cap housing said window in alignment with said optical axis and further having a longitudinal, hollow annulus portion projecting beyond said window for housing said pressure transducer.

3. The probe of claim 2 wherein said hollow annulus portion has arcuate inner and outer walls that define semi-circles in cross section and said pressure transducer is mounted flush against a backside surface of said inner sleeve wall.

4. The probe of claim 3 wherein said cap and said body are of stainless steel.

5. The probe of claim 1 wherein said window is a lens mounted at said forward end.

6. The probe of claim 5 wherein said lens is sapphire.

7. The probe of claim 1 and further comprising:
    means for operatively coupling a modulated light source to said optical fiber for transmitting modulated light through said body, out of a lens mounted at said forward end and into the sample along said optical axis; and
    measuring means operatively connected to said photoacoustic detection means for quantifying an acoustically detected response of said sample to said directed, modulated light.

8. The probe of claim 7 wherein said lens is acoustically isolated from said measuring means.

9. A system for photoacoustic detection of the concentration of an analyte in a sample, especially applicable for in situ chemical process monitoring of the sample, comprising:
    a hollow body having forward and rearward ends;
    a modulated light source;
    at least one fiber optic cable having one end operatively coupled to said modulated light source and extended through said body with an opposite end terminating within said body for conveying modulated light from said source through said body and into said sample along an optical axis when said forward end is placed in contact with said sample;
    a cap located at said forward end and having a window aligned with said optical axis to permit passage therethrough of modulated light into said sample;
    a hollow annulus sleeve portion of said cap projecting beyond said window and spaced laterally away from said optical axis;
    a piezoelectric transducer mounted within said sleeve for detecting an acoustic response of an analyte in said sample upon optical excitation thereof by said modulated light when said forward end is in contact therewith; and
    means for quantifying said acoustically detected response in order to obtain a value representative of the concentration of the analyte in the sample.

10. An apparatus for in situ detection of the concentration of an analyte in a sample, comprising:
    a hollow probe having forward and rearward ends;
    means for fiber optically directing modulated light from a modulated light source through said probe, beyond said forward end, and into said sample along an optical axis to optically excite a light absorbing analyte in said sample; and
    means for detecting an acoustic response of said optically excited sample, said detecting means extending through said probe beyond said forward end and spaced laterally away from said optical axis.

11. The apparatus of claim 10 and further comprising:
    a lens mounted at said forward end for transmission of modulated light therethrough into the sample; and
    means for isolating said detecting means from said lens.

12. A method of detecting the concentration of an analyte in a sample comprising the steps of:
    placing a forward end of an elongated probe body into contact with the sample;
    directing modulated light along said body via at least one optical fiber, outwardly of said body at its forward end and into said sample along an optical axis; and
    acoustically detecting, via a transducer housed within said probe, a photo-generated response of said sample to said directed modulated light.

13. The method of claim 12 and further comprising the steps of:
    generating an electrical signal corresponding to said acoustically detected response; and conveying said electrical signal rearwardly within said probe body and out of said rearward end.

14. The method of claim 13 and further comprising the steps of:
  inputting said electrical signal into a signal processor; and
  displaying a representation of said input electrical signal at said processor.

15. The method of claim 14 and further comprising the steps of:
  directing a portion of said modulated light from said source into contact with a photodiode;
  generating at said photodiode an electrical signal representative of power and frequency characteristics of said modulated light;
  inputting said generated signal into said signal processor for comparison with said electrical signal generated in response to said acoustical detection, thereby to obtain, by comparison of said input signals, a normalization value representative of the relationship between said concentration of said analyte in said sample and said detected response.

16. The method of claim 15 and further comprising the steps of:
  using said normalization value as a reference for comparison with a normalization value obtained from the photo excitation and acoustic detection of a second volume of the same sample having an unknown concentration of the same analyte, thereby to obtain a value representative of the concentration of the analyte in said second volume of said sample.

17. A method of preparing a sample having a desired concentration of analyte further comprising the steps of:
  a) placing a forward end of an elongated probe body into contact with a sample having a known concentrate of an analyte;
  b) directing modulated light along said body via at least one optical fiber, outwardly of said body at its forward end and into said sample along an optical axis;
  c) acoustically detecting, via a transducer housed within said probe, a photo-generated response of said sample to said directed modulated light;
  d) computing a reference normalization value representative of the relationship between said detected signal and said known sample concentration;
  e) directing a portion of said modulated light from said source into contact with a photodiode;
  f) generating at said photodiode an electrical signal representative of power and frequency characteristics of said modulated light;
  g) inputting said generated signal into said signal processor for comparison with said electrical signal generated in response to said acoustical detection, thereby to obtain, by comparison of said input signals, a normalization value representative of the relationship between said concentration of said analyte in said sample and said detected response;
  h) repeating steps a) through g) for additional samples having different, known analyte concentrations, thereby to obtain additional reference normalization values to establish a reference curve corresponding to the relationship between detected normalized values and actual concentration for a range of concentrations; and
  i) mixing the same analyte into another volume of the same sample, while using said probe and said photodiode to obtain a normalized value for said another volume, until said normalized value equals a value on said reference curve that corresponds to a desired concentration.

18. A method of preparing a second volume of a sample with an analyte equal in concentration to a first volume of the same sample with the same analyte, comprising the steps of:
  a) placing a forward end of a first elongated photoacoustic probe into the first volume of the sample with an analyte therein;
  b) optically exciting said sample via fiberoptic excitation means located at said forward end;
  c) detecting an acoustic response to said excitation via detection means located at said forward end;
  d) generating an electrical signal corresponding to said detected acoustic response;
  e) simultaneously performing steps a) through d) with a second photoacoustic probe on a second volume of the same sample having the same analyte; and
  f) adding more analyte to one of said volumes until the difference in value between said generated electric signals becomes zero.

* * * * *